US012728144B2

(12) United States Patent
Fougeres

(10) Patent No.: US 12,728,144 B2
(45) Date of Patent: Sep. 8, 2026

(54) COMPOSITION BASED ON NATURAL INGREDIENTS AND USE OF THE COMPOSITION FOR IMPROVING MENTAL HEALTH

(71) Applicant: Lydia Fougeres, Laval (CA)

(72) Inventor: Lydia Fougeres, Laval (CA)

( * ) Notice: Subject to any disclaimer, the term of this patent is extended or adjusted under 35 U.S.C. 154(b) by 771 days.

(21) Appl. No.: 17/854,151

(22) Filed: Jun. 30, 2022

(65) Prior Publication Data

US 2023/0310530 A1 Oct. 5, 2023

Related U.S. Application Data

(60) Provisional application No. 63/327,127, filed on Apr. 4, 2022.

(51) Int. Cl.

| | |
|---|---|
| ***A61K 36/282*** | (2006.01) |
| ***A61K 31/045*** | (2006.01) |
| ***A61K 36/185*** | (2006.01) |
| ***A61K 36/54*** | (2006.01) |
| ***A61K 36/61*** | (2006.01) |
| ***A61K 36/738*** | (2006.01) |
| ***A61K 36/752*** | (2006.01) |

(52) U.S. Cl.
CPC .......... *A61K 36/282* (2013.01); *A61K 31/045* (2013.01); *A61K 36/185* (2013.01); *A61K 36/54* (2013.01); *A61K 36/61* (2013.01); *A61K 36/738* (2013.01); *A61K 36/752* (2013.01)

(58) Field of Classification Search
CPC .. A61K 36/282; A61K 31/045; A61K 36/185; A61K 36/54; A61K 36/61; A61K 36/738; A61K 36/752; A61K 9/0014; A61K 36/537; A61K 47/10
See application file for complete search history.

(56) References Cited

PUBLICATIONS

Twisting the Leaf "Making 'Florida Water' at Home" (Sep. 19, 2019) retrieved from <URL: https://twisttheleaf.com/2019/09/16/making-florida-water-at-home/>, 5 pages. (Year: 2019).*
SilverBear "What is Florida Water and Why Do We Want It?" The Spells8 Forum. (Mar. 2020) retrieved from <URL: https://forum.spells8.com/t/what-is-florida-water-and-why-do-we-want-it/1257 >, 7 pages. (Year: 2020).*

* cited by examiner

*Primary Examiner* — Anand U Desai
*Assistant Examiner* — Robert Franklin Spaine
(74) *Attorney, Agent, or Firm* — Brennan, Manna & Diamond, LLC

(57) ABSTRACT

The present invention relates to a holistic healing composition made from natural ingredients for improving mental health and creating a positive environment. The composition includes liquids consisting of Vodka, Distilled Water, 90% pure alcohol; essential oils consisting of rose oil, lavender oil, tea tree oil, myrrh oil; herbs and flowers including fresh roses, sage, geranium flowers, cinnamon, Fresh Bay leave; lemon quarters, Himalayan salt, and orange peels. The composition is fermented for up to four months and rituals and prayers are performed on the composition to enhance quality and positive energy. In use, the composition is sprayed in the form of a mist onto a person or in an enclosed environment to create positive energy and/or to increase a person's Bovis units.

9 Claims, 2 Drawing Sheets

COMPOSITION BASED ON NATURAL INGREDIENTS AND USE OF THE COMPOSITION FOR IMPROVING MENTAL HEALTH

CROSS-REFERENCE TO RELATED APPLICATION

The present application claims priority to, and the benefit of, U.S. Provisional Application No. 63/327,127, which was filed on Apr. 4, 2022 and is incorporated herein by reference in its entirety.

FIELD OF THE INVENTION

The present invention relates generally to the field of human well-being and mental health. More specifically, the present invention relates to a novel holistic healing composition and associated method of production and use of composition. The composition is made from natural ingredients processed through a fermentation process for about four months and is enhanced by chanting prayers and performing rituals. The composition is sprayed in the form of a mist on an individual, in an enclosed space for more positive outlooks/outcomes. Accordingly, the present disclosure makes specific reference thereto. Nonetheless, it is to be appreciated that aspects of the present invention are also equally applicable to other like applications, devices, and methods of manufacture.

BACKGROUND

By way of background, well-being is fundamental to health and overall happiness of the individuals. Most of the individuals around the world suffer with stress, anxiety, depression, negative emotions, and many other factors that impact their physical, mental, emotional and social health. Individuals without a sense of well-being may not be able to focus on their day-to-day activities and may not be able to fully utilize their potential while working on various tasks. Some individuals may do meditation to promote their inner peace and calmness, and to reduce negative emotions. However, without being completely well, they may not be able to properly meditate or perform similar activities.

Some past incidents, traumatic situations, and more may haunt individuals throughout their life, that eventually degrade the mental health of the individuals and prevents them from overcoming negative emotions. Without a healthy mental status, individuals may lack focus and positive outlooks/outcomes on life and be looking to improve their worldview. Some individuals may be looking for methods to improve meditation and self-reflection. In order to become more focused in life, individuals may seek medical attention and get advice from psychologists and other medical specialists. However, medicines may not be suited for all the individuals and may have some side-effects. Also, many individuals may not be able to afford multiple visits to medical centers and may find medicines costly. Individuals may desire to obtain affordable solutions for improving their well-being.

Therefore, there exists a long felt need in the art for a solution that improves the worldview of individuals plagued with stress, anxiety, and other similar emotions. There is also a long felt need in the art for a solution that is easy to use and is affordable by all the individuals. Additionally, there is a long felt need in the art for a healing solution that can be easily used by individuals without having any side-effects.

Moreover, there is a long felt need in the art for a healing solution that enables the individuals to become more focused and to obtain a positive outlook on life. Further, there is a long felt need in the art for a healing solution that improves mental health and creates positive outlooks/outcomes, while enabling the individuals to forget any traumatic incidents and overcome negative situations in life. Furthermore, there is a long felt need in the art for a healing spray solution that improves physical and mental well-being of individuals and ensures a happy and focused life. Finally, there is a long felt need in the art for a holistic healing solution that is easy to store and obviates the need to seek medical advice for well-being of individuals.

The subject matter disclosed and claimed herein, in one embodiment thereof, comprises a composition for improving mental health and for creating a positive atmosphere. The composition is sprayed in the form of a mist to create a soothing effect and to release positive energy, and further comprising a liquid medium consisting of vodka, distilled water, and alcohol; essential oils consisting of rose oil, lavender oil, tea tree oil, myrrh oil; a plurality of fresh flowers including roses, sage, geranium, cinnamon, bay leaves; Himalayan salt; and, lemon quarters and orange peels wherein the composition is fermented for a period of time (i.e. about four months) and is exposed to ephemeral prayers and rituals during fermentation for imbibing positive energy.

In this manner, the healing composition and associated method of manufacturing healing composition of the present invention accomplishes all of the forgoing objectives and provides users a holistic healing spray for improving mental health and for creating positive outlooks/outcomes. The natural ingredients, rituals, and prayers during production of the composition help in elevating vibrational energy, improving mental health that can be measured in Bovis units. The composition can be sprayed in the form of a mist easily to release positive energy.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a method for improving mental health of a person and creating positive outlooks/outcomes. The method further comprising the steps of spraying a healing solution in the form of a mist on the person, the healing solution having a composition consisting of natural ingredients including natural flowers, a plurality of essential oils, a plurality of herbs and spices, Himalayan salt, vodka, distilled water and 90% pure alcohol wherein the composition is fermented for a period of time (i.e. up to four months) for forming the healing solution and ephemeral prayers and rituals are performed on the composition during the process of fermentation. The fermentation takes place at room temperature in a closed container or jar.

In yet another embodiment, the method further includes the step of spraying the mist at a dosage enough to improve mental health of the person.

In yet another embodiment, the method further includes spraying mist using an aerosol bottle.

In yet another embodiment, a method of making a holistic healing composition for improving mental health and creating positive environment is described. The method comprising mixing a plurality of natural ingredients including a plurality of fresh flowers, a plurality of essential oils, a plurality of herbs and spices, a quantity of Himalayan salt, vodka, distilled water and 90% pure alcohol; adding lemon quarters and orange peels to said mixture formed by mixing of natural ingredients; fermenting the resultant mixture for a period of time (i.e. up to four months); reciting prayers and performing rituals to enhance positive quality of the fermenting mixture during the process of fermentation wherein the amounts or levels of said natural ingredients are associated to produce a desired healing effect.

In yet another embodiment, a composition for improving mental health and creating positive atmosphere is disclosed. The composition includes a liquid medium consisting of vodka, distilled water, and alcohol; essential oils consisting of rose oil, lavender oil, tea tree oil, myrrh oil; a plurality of fresh flowers including roses, sage, geranium, cinnamon, bay leaves; Himalayan salt; lemon quarters and orange peels wherein the composition is fermented for up to four months and is exposed to ephemeral prayers and rituals during fermentation for imbibing positive energy.

In yet another embodiment, the healing solution can increase the Bovis unit of a person from 7000 units to 12000 units.

In yet another embodiment, the liquid medium can have from about 35% to about 50% vodka, from about 35% to about 50% distilled water, and from about 10% to about 30% of 90% pure alcohol.

In yet another embodiment, the essential oils can include, in one exemplary configuration, about 38% Rose oil by weight, 10% Lavender oil by weight, 38% Tea tree oil by weight, and 14% Myrrh oil by weight.

In yet another embodiment, the herbs and flowers can include, in one exemplary configuration, about 41% Fresh roses by weight, 8.3% Fresh sage by weight, 41.66% Fresh Geranium flowers by weight, 4.16% Cinnamon by weight, and 4.16% Fresh Bay leaves by weight.

Numerous benefits and advantages of this invention will become apparent to those skilled in the art to which it pertains upon reading and understanding of the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
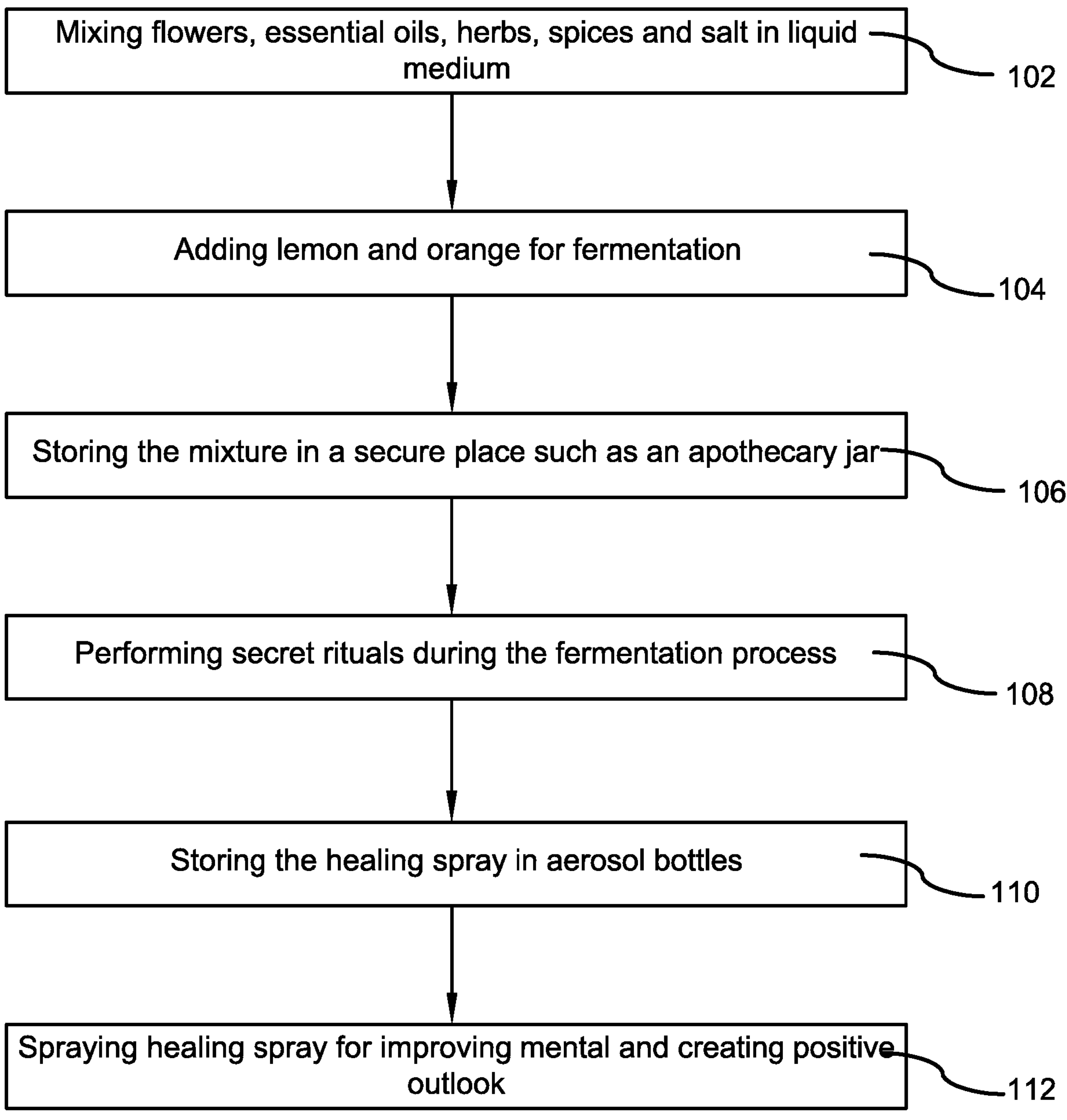
FIG. 1 illustrates a flow chart depicting a process of making and using the holistic healing spray of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long felt need in the art for a solution that improves the worldview of individuals plagued with stress, anxiety, and other similar emotions. There is also a long felt need in the art for a solution that is easy to use and is affordable by all the individuals. Additionally, there is a long felt need in the art for a healing solution that can be easily used by individuals without having any side-effects. Moreover, there is a long felt need in the art for a healing solution that enables the individuals to become more focused and to obtain a positive outlook on life. Further, there is a long felt need in the art for a healing solution that improves mental health and creates positive outlooks/outcomes, while enabling the individuals to forget any traumatic incidents and overcome negative situations in life. Furthermore, there is a long felt need in the art for a healing spray solution that improves physical and mental well-being of individuals and ensures a happy and focused life. Finally, there is a long felt need in the art for a holistic healing solution that is easy to store and obviates the need to seek medical advice for well-being of individuals.

The present invention, in one exemplary embodiment, is a method for improving mental health of a person and creating positive outlooks/outcomes. The method further comprising the steps of spraying a healing solution in the form of a mist on the person, the healing solution having a composition consisting of natural ingredients including natural flowers, a plurality of essential oils, a plurality of herbs and spices, Himalayan salt, vodka, distilled water and 90% pure alcohol wherein the composition is fermented for up to four months for forming the healing solution.

In accordance with the present invention, the holistic healing spray is configured for improving mental health and creating positive outlooks/outcomes. The spray uses natural ingredients that are fermented up to four months that helps in creating soothing effects from the healing spray. The healing spray composition is a stable formulation and remains liquid at room temperature. The formulation features flowers, essential oils, herbs and spices, salt, and vodka fermented up to four months. The holistic healing spray can be used by individuals to elevate positive vibrational energy, improve mental health, and create positive outlook. The formulation can be sprayed in the form of a mist using a mist bottle in which the spray is commercially available for consumers. The spray also provides anxiety and stress relief, energy calmness, and functions as a natural anti-depressant and relationship enhancer.

A liquid medium including vodka, distilled water, and 90% pure iso-propyl alcohol is used for forming the healing spray. Vodka has inherent antiseptic features that can destroy pathogens. Distilled water provides an aqua media for the healing spray and helps in providing a mist spray. Pure alcohol helps in creating feeling of relaxation and is an ingredient of the healing spray.

A plurality of essential oils is included in the formulation of the healing spray. More specifically, rose oil, lavender oil, tea tree oil, and myrrh oil are used in the healing spray. The rose oil helps in building confidence and enhancements of mood. The lavender oil is an anti-bacterial floral essential oil having the ability to calm stress and promote sleep. The tea tree oil possesses therapeutic properties and is a component of mental health aromatherapy. Further, the tea tree oil is antibacterial, anti-inflammatory, antiviral, and antifungal. Myrrh oil provides relief from pain and anxiety. The sedative scent of Myrrh helps in stabilizing emotions, lifting negative moods, promoting the feeling of being grounded, releasing childhood trauma and PTSD, and encouraging the feeling of spiritual awakening.

A plurality of herbs and flowers are mixed with the essential oils in the liquid medium for fermentation to produce the mental healing spray of the present invention. Fresh roses are used for providing fragrance and positive impact. Fresh sage which can be a combination of white sage, heavenly sage, and clary sage is used for clearing energy and helps in purifying the soul.

Fresh geranium flowers are included in preparation of the healing spray as their warm, rosy smell is uplifting, energizing, and inspiring. Geranium flowers also help in releasing stress, has antidepressant, sedative, anxiety-reducing, and muscle-relaxing properties. Cinnamon is included in the spray as cinnamon is believed to bring good luck and spiritual protection. Cinnamon can be used in the form of cinnamon leaves or powdered cinnamon. Fresh bay leaves are included as they help in relieving anxiety. Research has shown that bay leaves can also be used to treat diabetes and migraine headaches. The American Association of Nurse Anesthetists also acknowledges bay leaves are a great stress reliever.

Himalayan salt is included in the formulation of the healing spray as it helps in improving mental clarity. Himalayan salt is known to help uplift the mood for those who are affected by depression and chronic fatigue and has been used as natural treatments for migraine headaches, and other mental diseases.

For the formation of the holistic healing spray, all the above mentioned natural and toxin free ingredients are mixed and fermented for up to four months. Further, during the fermentation process, rituals, and ephemeral prayers are performed to enhance the value and quality of the spray. The fermented spray is then stored in mist bottles and can be used by individuals for spraying to prepare a space for healing work, to clear out the energy of illness in a sick room and for uplifting mood, energizing, and anxiety relief benefits.

Orange peels are used as raw material for fermentation and helps in forming yeast and breakdown of the ingredients of the spray. Additionally, lemon peels are used for facilitating fermentation to product the misting healing spray in four months.

Table 1 below shows approximate concentrations or amounts or levels of various natural ingredients in the formulation of holistic healing spray.

TABLE 1

| Ingredients | Composition in percentage by weight (% w/w) |
|---|---|
| Liquids | 35-60 |
| Essential oils | 10-30 |
| Herbs and Flowers | 25-45 |
| Himalayan salt | 2-8 |

In one exemplary embodiment, the liquids forming the liquid medium of the spray comprises of about 50% of the formulation. In other embodiments, the liquids can be about 35%, 40%, 55%, 60% by weight in the formulation.

Table 2 below shows approximate concentrations of composition or amounts or levels forming the liquids ingredient of holistic healing spray.

TABLE 2

| Ingredients | Composition in percentage by weight (% w/w) |
|---|---|
| Vodka | 35-50 |
| Distilled Water | 35-50 |
| 90% pure alcohol | 10-30 |

In exemplary arrangements, the vodka is from about 35% to about 50%, distilled water is from about 35% to about 50%, and 90% pure alcohol is from about 10% to about 30% in the liquid ingredients. In other embodiments, the vodka can be about 35%, 45%, 50% by weight.

Table 3 below shows approximate concentrations or amounts or levels of individual essential oils forming the essential oil component of the holistic healing spray.

TABLE 3

| Ingredients | Composition in percentage by weight (% w/w) |
|---|---|
| Rose oil | 30-46 |
| Lavender oil | 5-15 |
| Tea tree oil | 30-46 |
| Myrrh oil | 8-20 |

It should be noted that any other essential oils can be added to the healing spray as per preferences of a user. Essential oils are formed from leaves and stems of plants and distillation of the aromatic plants is done to form the essential oils.

Table 4 below shows approximate concentrations or amounts or levels of individual flowers and herbs forming the herbs and flowers ingredient component of the holistic healing spray.

TABLE 4

| Ingredients | Composition in percentage by weight (% w/w) |
|---|---|
| Fresh roses | 30-50 |
| Fresh sage | 4-12 |
| Fresh Geranium flowers | 30-50 |
| Cinnamon | 2-6 |
| Fresh bay leaves | 2-6 |

All the flowers and herbs are natural and fresh used without any chemical processing in the healing spray. Further, in the preferred embodiment, the petals of the flowers are included in the fermentation process. Alternatively, flowers and herbs in powdered form can be included in the spray.

In one exemplary embodiment, a plastic bottle with an aperture or opening dimensioned to aerosolize the healing spray formulation by forming a spray is used for spraying the healing spray. The nozzle opening is usually found in the top of the bottle and is coupled to a pipe for carrying the healing spray to the nozzle.

FIG. 1 illustrates a flow chart 100 depicting a process of making and using the holistic healing spray of the present invention in accordance with the disclosed architecture. Initially, for preparing the holistic healing formulation, fresh flowers, essential oils, herbs, spices, and Himalayan salt are mixed in a liquid medium wherein the liquid medium is formed using vodka, distilled water, and alcohol (Step 102). Then, lemon quarters and orange peels are added to the mixture to facilitate fermentation of the mixture (Step 104). For fermentation to take place, the mixture is stored in a secure place such as an apothecary jar (Step 106).

For enhancing quality and infusing positivity in the mixture during the fermentation process, secret rituals and ephemeral prayers are performed for four months during the which the holistic healing mist is formed (Step 108). After the fermentation process has been completed (i.e. from two to four months), the healing solution is stored in aerosol bottles for use by consumers (Step 110). Finally, the healing formulation is sprayed in the form of mist at a target in an enclosed area in order to improve mental health and to create a positive environment and outlook (Step 112).

Figure 2:
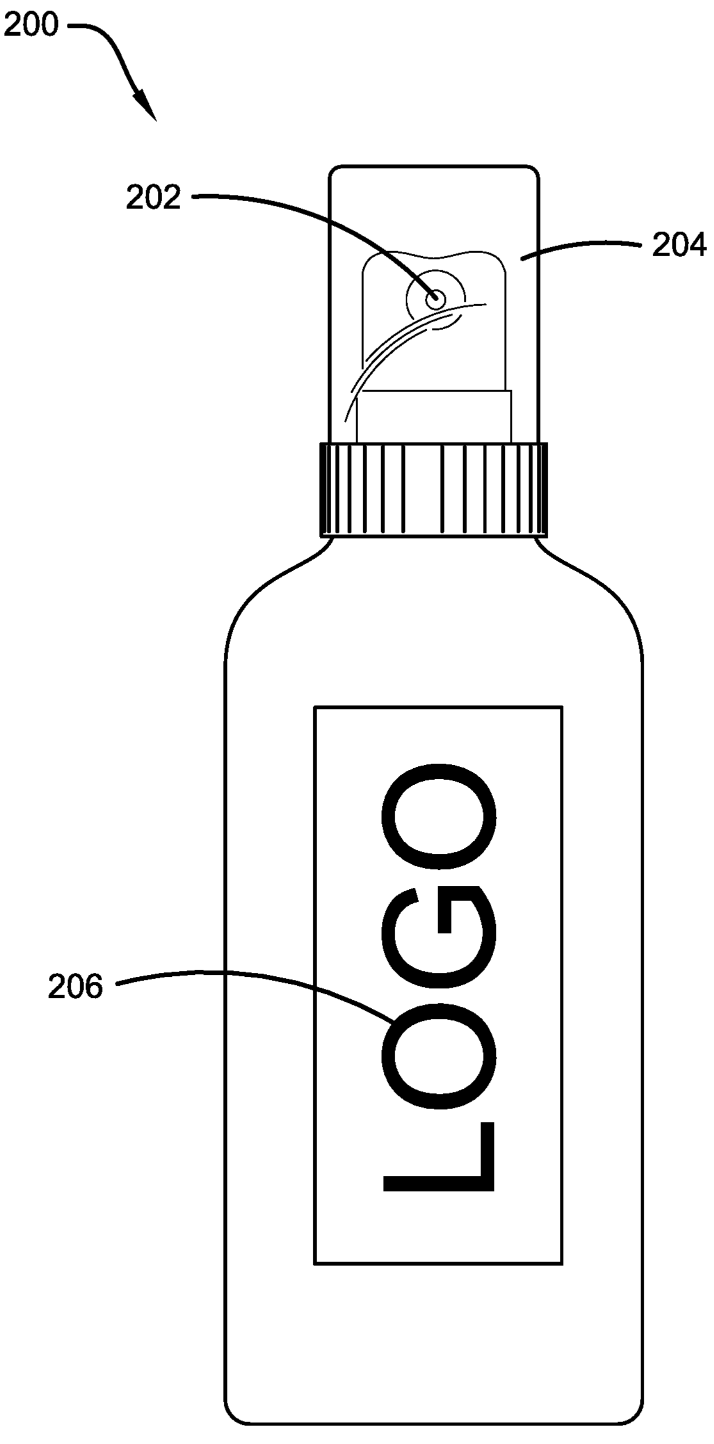
FIG. 2 illustrates an exemplary aerosol bottle for spraying mist of the holistic healing solution of the present invention in accordance with the disclosed architecture.

FIG. 2 illustrates an exemplary aerosol bottle for spraying mist of the holistic healing solution of the present invention in accordance with the disclosed architecture. The aerosol bottle 200 is configured to produce a mist of the healing solution of the present invention allowing easy spraying at any target area for creating positive energy. The exemplary bottle 200 has nozzle spray 202 configured to release the mist of the healing solution. The nozzle 202 is protected by a cover/lid 204 which is removably placed on the bottle.

The bottle 200 may have a logo 206 for branding and marketing purposes. The bottle 200 may also have a label disposed thereon illustrating the ingredients of the healing solution stored in the bottle. The bottle 200 may come in variety of sizes, shapes, and designs. The healing solution can be available in bottles having a volume from about 30 ml to about 500 ml to meet requirements of different users.

The healing solution of the present invention improves life energy which can be measured in Bovis units. In short, Bovis units are a unit of measurement for life energy (also known to many as Prana or Chi). The origin of this value lies, as is so often the case, in the research of a scientist after whose name it was named. The Frenchman Alfred Bovis was a physicist and lived from 1871 to 1947. Thanks to Bovis' research, it is now possible to record the life energy in values. The recording of the vital energy of food is of great importance and also the vital radiation in the human being itself is of particular importance. It is also important, for example, to measure the Bovis units of substances with which our body comes into contact in order to get a picture of the influences they have on our body. The healing solution, when misted upon a person, can increase the Bovis units of the person, in one example, from 7000 units to 12000 units within 15 days of use (i.e. an increase of at least 7000 units).

The healing composition of the present invention can be designed to be short-acting, fast-releasing, long-acting, or sustained-releasing as described herein. Thus, the formulations may also be formulated for controlled release or for slow release. Individuals of all ages and genders are positively impacted by the healing solution.

The product comprising the present formulation is a disruptive product, as it is practically used for positive outlook and mental health improvement which can represent savings in the cost of a treatment and improve quality of life. Further, the healing composition of the present invention is pharmacologically acceptable.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "holistic healing solution", "healing solution", "holistic healing composition", and "composition" are interchangeable and refer to the holistic healing composition of the present invention for sunglasses.

The terms "comprising," "including," "having," and the like are used interchangeably and have the same meaning. Similarly, "comprises," "includes," "has," and the like are used interchangeably and have the same meaning. The phrases "pharmaceutically acceptable" or "pharmacologically acceptable" refer to molecular entities and compositions that do not produce adverse, allergic, or other untoward reactions when administered to an animal or a human.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of forming a holistic healing composition comprising the steps of:

supplying a liquid medium comprising a vodka comprising 35% by weight of the liquid medium, a distilled water comprising 35% by weight of the liquid medium, and a 90% pure iso-propyl alcohol comprising 30% by weight of the liquid medium;

adding at least one essential oil, an herb, a flower, a spice, a Himalayan salt, a lemon, and an orange peel to said liquid medium to form a healing composition;

storing said healing composition in an apothecary jar; and storing said healing composition in said apothecary jar for four months; and pouring said stored healing composition into a 100 mL aerosol bottle comprising a nozzle spray, a cover for protecting the nozzle spray, and a logo indicium.

2. The method of claim 1, wherein said at least one essential oil is selected from a group consisting of a rose oil, a lavender oil, a tea tree oil and a myrrh oil.

3. The method of claim 2, wherein said herb is selected from a group consisting of a sage and a bay leaf.

4. The method of claim 3, wherein said flower is selected from a group consisting of a rose and a geranium.

5. The method of claim 4, wherein said spice is a cinnamon.

6. The method of claim 1, wherein said stored healing composition comprises said liquid medium from 35% to 60% percentage by weight, said at least one essential oil from 10% to 30% percentage by weight, said herb and said flower from 25% to 45% percentage by weight, and said Himalayan salt from 2% to 8% percentage by weight.

7. A method of forming a holistic healing composition comprising the steps of:

supplying a liquid medium comprising a vodka comprising 40% by weight of the liquid medium, a distilled water comprising 40% by weight of the liquid medium, and a 90% pure iso-propyl alcohol comprising 20% by weight of the liquid medium;

adding at least one essential oil, an herb, a flower, a spice, a Himalayan salt, a lemon quarter and an orange peel to said liquid medium to form a healing composition;

storing said healing composition in a container; and storing said healing composition in said container for four months;

wherein said stored healing composition comprises said liquid medium from 35% to 60% percentage by weight, said at least one essential oil from 10% to 30% percentage by weight, said herb and said flower from 25% to 45% percentage by weight, and said Himalayan salt from 2% to 8% percentage by weight; and pouring said stored healing composition into a 500 mL aerosol bottle comprising a nozzle spray, a cover for protecting the nozzle spray, and a logo indicium.

8. A method of forming a holistic healing composition comprising the steps of:

supplying a liquid medium comprising a vodka comprising 45% by weight of the liquid medium, a distilled water comprising 45% by weight of the liquid medium, and an iso-propyl alcohol comprising 10% by weight of the liquid medium;

adding essential oils, herbs, flowers, spice, Himalayan salt, lemon quarters, and orange peels to said liquid medium to form a healing composition;

storing said healing composition in a container; and storing said healing composition in said container for four months; and pouring said stored healing composition into a 30 mL aerosol bottle comprising a nozzle spray, a cover for protecting the nozzle spray, and a logo indicium; and wherein said essential oils are selected from a group consisting of a rose oil, a lavender oil, a tea tree oil, and a myrrh oil; and wherein said herbs are selected from a group consisting of a sage and a bay leaf.

9. The method of claim 8, wherein said stored healing composition comprises said liquid medium from 35% to 60% percentage by weight, said essential oils from 10% to 30% percentage by weight, said herbs and said flowers from 25% to 45% percentage by weight, and said Himalayan salt from 2% to 8% percentage by weight.

* * * * *